United States Patent
Gruetzmacher et al.

(10) Patent No.: US 10,023,675 B2
(45) Date of Patent: *Jul. 17, 2018

(54) POLYMER NANOPARTICLES

(71) Applicant: ETH ZUERICH, Zurich (CH)

(72) Inventors: Hansjoerg Gruetzmacher, Dielsdorf (CH); Timo Ott, Duisburg (DE)

(73) Assignee: ETH ZUERICH, Zurich (CH)

( * ) Notice: Subject to any disclaimer, the term of this patent is extended or adjusted under 35 U.S.C. 154(b) by 160 days.

This patent is subject to a terminal disclaimer.

(21) Appl. No.: 14/872,148

(22) Filed: Oct. 1, 2015

(65) Prior Publication Data

US 2016/0024241 A1    Jan. 28, 2016

Related U.S. Application Data

(62) Division of application No. 13/264,991, filed as application No. PCT/CH2010/000103 on Apr. 16, 2010, now Pat. No. 9,181,358.

(30) Foreign Application Priority Data

Apr. 20, 2009   (CH) .................................... 618/09

(51) Int. Cl.
| | |
|---|---|
| *C08F 228/02* | (2006.01) |
| *C07F 9/50* | (2006.01) |
| *C08F 2/50* | (2006.01) |
| *C07F 9/53* | (2006.01) |
| *C07F 9/59* | (2006.01) |
| *C07F 9/6506* | (2006.01) |
| *C08F 2/24* | (2006.01) |
| *C08F 112/08* | (2006.01) |
| *C08F 122/10* | (2006.01) |
| *C08F 212/08* | (2006.01) |
| *C08F 222/30* | (2006.01) |

(52) U.S. Cl.
CPC .......... *C08F 228/02* (2013.01); *C07F 9/5036* (2013.01); *C07F 9/5045* (2013.01); *C07F 9/5337* (2013.01); *C07F 9/591* (2013.01); *C07F 9/65061* (2013.01); *C07F 9/65062* (2013.01); *C08F 2/24* (2013.01); *C08F 2/50* (2013.01); *C08F 112/08* (2013.01); *C08F 122/10* (2013.01); *C08F 212/08* (2013.01); *C08F 222/30* (2013.01)

(58) Field of Classification Search
CPC .... C08F 228/02; C08F 212/08; C08F 122/10; C08F 112/08; C08F 222/30; C08F 2/50; C08F 2/24; C07F 9/65062; C07F 9/65061; C07F 9/591; C07F 9/5337; C07F 9/5045; C07F 9/5036
See application file for complete search history.

(56) References Cited

U.S. PATENT DOCUMENTS

| | | |
|---|---|---|
| 4,792,632 A | 12/1988 | Ellrich et al. |
| 6,020,528 A | 2/2000 | Leppard et al. |
| 2002/0107413 A1 | 8/2002 | Wolf et al. |
| 2004/0204613 A1 | 10/2004 | Wolf et al. |
| 2006/0004116 A1 | 1/2006 | Kishi et al. |
| 2006/0247436 A1 | 11/2006 | Sommerlade et al. |
| 2006/0287416 A1 | 12/2006 | Schellenberg et al. |
| 2008/0004464 A1 | 1/2008 | Murer et al. |
| 2008/0071115 A1 | 3/2008 | Sommerlade et al. |
| 2010/0234484 A1 | 9/2010 | Schellenberg et al. |

FOREIGN PATENT DOCUMENTS

| | | |
|---|---|---|
| EP | 1 734 088 A1 | 12/2006 |
| GB | 2 310 855 A | 9/1997 |
| WO | WO 03/019295 A1 | 3/2003 |
| WO | WO 2005/014605 A1 | 2/2005 |
| WO | WO 2005/023878 A1 | 3/2005 |
| WO | WO 2006/056541 A1 | 6/2006 |
| WO | WO 2006/074983 A1 | 7/2006 |
| WO | WO 2008/003601 A1 | 1/2008 |

OTHER PUBLICATIONS

S. Nozari et al.: "RAFT Agent Concentration in Polymer Particles during Emulsion Polymerization", Macromolecules 2005, 38, pp. 10449-10454 (Nov. 17, 2005).

S. Wang et al.: "Preparation of polystyrene particles with narrow particle size distribution by γ-ray initiated miniemulsion polymerization stabilized by polymeric surfactant", European Polymer Journal, 43, pp. 178-184 (2007).

P. Kuo et al.: "Photoinitiated Poymerization of Styrene in Microemulsions", Macromolecules 1987, 20, pp. 1216-1221 (1987).

*Primary Examiner* — Michael F Pepitone
*Assistant Examiner* — Jessica M Roswell
(74) *Attorney, Agent, or Firm* — Norman B. Thot

(57) ABSTRACT

A process for the preparation of a polymer nanoparticle by a photoinduced emulsion polymerization includes preparing an emulsion comprising at least one surfactant, a dispersed phase and a continuous phase. The dispersed phase comprises at least one polymerizable monomer and the continuous phase comprises water and at least one photoinitiator. The at least one polymerizable monomer is polymerized by exposing the emulsion to an electromagnetic radiation having a wavelength so as to induce a generation of radicals from the at least one photoinitiator. The at least one photoinitiator is selected from at least one compound of formula (I)

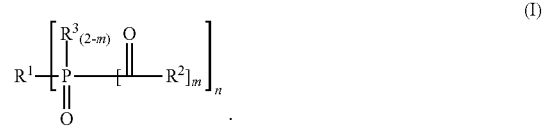

(I)

1 Claim, No Drawings

POLYMER NANOPARTICLES

CROSS REFERENCE TO PRIOR APPLICATIONS

This application is a divisional of U.S. application Ser. No. 13/264,991, filed on Jan. 17, 2012. U.S. application Ser. No. 13/264,991 is a U.S National Phase application under 35 U.S.C. § 371 of International Application No. PCT/CH2010/000103, filed on Apr. 16, 2010, and which claims benefit to Swiss Patent Application No. 618/09, filed on Apr. 20, 2009. The International Application was published in English on Oct. 28, 2010 as WO 2010/121387 A1 under PCT Article 21(2).

FIELD

The present invention relates to polymer nanoparticles with a low polydispersity and a photo-induced process for the preparation of such polymer nanoparticles. The present invention further relates to novel photoinitiators suitable for carrying out said process.

BACKGROUND

Polymer particles are widely used as coating, adhesive, ink and painting materials, for precision mold constructions and the manufacture of micro-sized materials. The unique properties of micro- and nanoscaled polymer particles with low polydispersities have meanwhile gained significant attention not only in the electronics industry, for example, in the manufacture of TFT and LCD displays, digital toners and e-paper, but also in the medical sector such as for drug delivery systems, diagnostic sensors, contrast agents and many other fields of industry.

Polymer nanoparticles are frequently synthesized by physical methods such as the evaporation of polymer solution droplets or by the direct synthesis of the nanoparticles using special polymerisation processes. The most common processes are radical polymerisations such as suspension polymerizations and emulsion polymerizations.

Over the last decades, a number of radical polymerization processes were developed in order to achieve a better control over the polymerisation process and thus the properties of the resulting polymer nanoparticles.

S. Nozari et al. (Macromolecules 2005, 38, 10449) describes a RAFT (reversible addition fragmentation transfer) emulsion polymerization process for the preparation of polystyrene nanoparticles using dithioic acids as sur-inifer-ters, thereby obtaining polystyrene with an polydispersity index ($M_w/M_n$), hereinafter also referred to as M-PDI, of 1.22 to 1.31, and a weight average molar mass of 110 to 170 kg/mol.

Emulsion polymerisations induced by X-ray radiation are described in S. Wang, X. Wang, Z. Zhang, Eur. Polym. J., 2007, 43, 178.

Emulsion polymerisations induced by UV/Vis radiation are described in P. Kuo, N. Turro, Macromolekules 1987, 20, 1216-1221, wherein the formation of polystyrene nanoparticles having a M-PDI of 1.6 to 2.2 and a weight average molecular weight of 500 kg/mol or less.

The industrial applicability of the processes described above is, however, hampered due to the use of toxic, expensive, coloured or malodorant chemicals such as heavy metal salts, sulphur containing compounds and stable radicals such as 2,2,6,6-tetramethylpiperidine-1-oxyl (TEMPO).

SUMMARY

An aspect of the present invention is to provide a process for the preparation of polymer nanoparticles having a low polydispersity while simultaneously allowing for the easy control of the particle size.

In an embodiment, the present invention provides a process for the preparation of a polymer nanoparticle by a photoinduced emulsion polymerization which includes preparing an emulsion comprising at least one surfactant, a dispersed phase and a continuous phase. The dispersed phase comprises at least one polymerizable monomer and the continuous phase comprises water and at least one photoinitiator. The at least one polymerizable monomer is polymerized by exposing the emulsion to an electromagnetic radiation having a wavelength so as to induce a generation of radicals from the at least one photoinitiator. The at least one photoinitiator is selected from at least one compound of formula (I):

wherein
n is 1 or 2,
m is 1 or 2,
$R^1$, if n=1 is $C_6$-$C_{14}$-aryl or heterocyclyl or
is at least one of $C_1$-$C_{18}$-alkoxy, $-N(R^4)_2$, $C_1$-$C_{18}$-alkyl, $C_2$-$C_{18}$-alkenyl, and $C_7$-$C_{20}$-arylalkyl, wherein the at least one of $C_1$-$C_{18}$-alkoxy, $-N(R^4)_2$, $C_1$-$C_{18}$-alkyl, $C_2$-$C_{18}$-alkenyl, and $C_7$-$C_{20}$-arylalkyl is
not, once, twice or more than twice interrupted by non-successive functional groups selected from the group consisting of —O—, —S—, —$SO_2$—, —SO—, —$SO_2NR^4$—, $NR^4SO_2$—, —$NR^4$—, —$N^+(R^4)_2An^-$—, —CO—, —O(CO)—, (CO)O—, —O(CO)O—, —$NR^4(CO)NR^4$—, $NR^4$(CO)—, —(CO)$NR^4$—, —$NR^4$(CO)O—, —O(CO)$NR^4$—, —Si($R^5$)$_2$—, —OSi($R^5$)$_2$—, —OSi($R^5$)$_2$O—, —Si($R^5$)$_2$O—,
is not, once, twice or more than twice interrupted by bivalent residues selected from the group consisting of heterocyclo-diyl, heterocyclo-diylium$^+$An$^-$ and $C_6$-$C_{14}$-aryldiyl, and is not, additionally or alternatively either once, twice or more than twice substituted by substituents selected from the group consisting of halogen, cyano, azido, epoxy, $C_6$-$C_{14}$-aryl, $C_1$-$C_8$-alkyl, $C_1$-$C_8$-alkoxy, $C_2$-$C_8$-alkenyl, $C_1$-$C_8$-alkylthio, $C_7$-$C_{20}$-arylalkyl, hydroxy, —$SO_3M$, —COOM, $PO_3M_2$, —PO(N($R^5$)$_2$)$_2$, PO(O$R^5$)$_2$, —$SO_2N(R^4)_2$, —$N(R^4)_2$, —$N^+(R^4)_3An^-$, heterocyclylium$^+$An$^-$, —$CO_2N$($R^5$)$_2$, —$COR^4$, —$OCOR^4$, —$NR^4$(CO)$R^5$, —(CO)O$R^4$, —$NR^4$(CO)N($R^4$)$_2$, —Si(O$R^5$)$_y$($R^5$)$_{3-y}$, and —OSi(O$R^5$)$_y$($R^5$)$_{3-y}$, with y=1, 2 or 3,
$R^1$, if n=2 is $C_6$-$C_{15}$-aryldiyl or
is at least one of $C_4$-$C_{18}$-alkanediyl, $C_4$-$C_{18}$-alkenediyl, and $C_4$-$C_{18}$-alkinediyl, wherein the at least one of $C_4$-$C_{18}$-alkanediyl, $C_4$-$C_{18}$-alkenediyl, and $C_4$-$C_{18}$-alkinediyl is not, once, twice or more than twice interrupted by non-successive groups selected from the group consisting of —O—, —SO$_2$—, —NR$^4$—, —N$^+$(R$^4$)$_2$An$^-$—, —CO—, —OCO—, —O(CO)O—, NR$^4$(CO)—, —NR$^4$(CO)O—, O(CO)NR$^4$—, —NR$^4$(CO)NR$^4$—, C$_6$-C$_{15}$-aryl, heterocyclo-diyl and heterocyclo-diylium$^+$An$^-$, is not, additionally or alternatively either once, twice or more than twice substituted by substituents selected from the group consisting of halogen, cyano, C$_6$-C$_{14}$-aryl, heterocyclyl, heterocyclo-diylium$^+$An$^-$, C$_1$-C$_8$-alkyl, C$_1$-C$_8$-alkoxy, C$_1$-C$_8$-alkylthio, —SO$_3$M, —COOM, PO$_3$M$_2$, —N(R$^4$)$_2$, —N$^+$(R$^4$)$_3$An$^-$, —CO$_2$N(R$^4$)$_2$, —OCOR$^4$—, —O(CO)OR$^4$—, NR$^4$(CO)R$^5$, —NR$^3$(CO)OR$^5$, O(CO)N(R$^4$)$_2$, —NR$^4$(CO)N(R$^4$)$_2$, or is bivalent bis(C$_6$-C$_{1s}$)-aryl, which is either not or once interrupted by groups selected from the group consisting of —O—, —S—, C$_4$-C$_{18}$-alkanediyl, and C$_4$-C$_{18}$-alkenediyl, R$^2$ is C$_6$-C$_{14}$-aryl or heterocyclyl or is at least one of C$_1$-C$_{18}$-alkyl, C$_2$-C$_{18}$-alkenyl, and C$_7$-C$_{20}$-arylalkyl, wherein the at least one of C$_1$-C$_{18}$-alkyl, C$_2$-C$_{18}$-alkenyl, and C$_7$-C$_{20}$-arylalkyl is is not, once, twice or more than twice interrupted by non-successive functional groups selected from the group consisting of —O—, —NR$^4$—, —N$^+$(R$^4$)$_2$An$^-$—, —CO—, —OCO—, —O(CO)O—, NR$^4$(CO)—, —NR$^4$(CO)O—, O(CO)NR$^4$—, and —NR$^4$(CO)NR$^4$—, is not, once, twice or more than twice interrupted by bivalent residues selected from the group consisting of heterocyclo-diyl, heterocyclo-diylium$^+$An$^-$, and C$_6$-C$_{14}$-aryldiyl, and not, additionally or alternatively either once, twice or more than twice substituted by substituents selected from the group consisting of halogen, cyano, C$_6$-C$_{14}$-aryl; heterocyclyl, C$_1$-C$_8$-alkyl, C$_1$-C$_8$-alkoxy, C$_1$-C$_8$-alkylthio, C$_2$-C$_8$-alkenyl, C$_4$-C$_{15}$-arylalkyl, —COOM, —SO$_3$M, —PO$_3$M$_2$, —SO$_2$N(R$^4$)$_2$, —NR$^4$SO$_2$R$^5$, —N(R$^4$)$_2$—, —N$^+$(R$^4$)$_3$An$^-$, —CO$_2$N(R$^4$)$_2$, —COR$^4$—, —OCOR$^5$, —O(CO)OR$^5$, NR$^4$(CO)R$^4$, —NR$^4$(CO)OR$^4$, O(CO)N(R$^4$)$_2$, and —NR$^4$(CO)N(R$^4$)$_2$, R$^3$ independently denotes a substituent as defined for R$^1$ if n is 1, whereby R$^4$ is independently selected from the group consisting of hydrogen, C$_1$-C$_8$-alkyl, C$_6$-C$_{14}$-aryl, C$_7$-C$_{15}$-arylalkyl and heterocyclyl, or N(R$^4$)$_2$ as a whole is a N-containing heterocycle, or N$^+$(R$^4$)$_2$An$^-$ and N$^+$(R$^4$)$_3$An$^-$ as a whole are or contain a cationic N-containing heterocycle with a counteranion, R$^5$ is independently selected from the group consisting of C$_1$-C$_8$-alkyl, C$_6$-C$_{14}$-aryl, C$_7$-C$_{15}$-arylalkyl and heterocyclyl, or N(R$^5$)$_2$ as a whole is a N-containing heterocycle or N$^+$(R$^5$)$_2$An$^-$ and N$^+$(R$^5$)$_3$An$^-$ as a whole are or contain a cationic N-containing heterocycle with a counteranion, M is hydrogen, or an 1/q equivalent of a q-valent metal ion, or is an ammonium ion, or a primary, secondary, tertiary or quaternary organic ammonium ion, or a guanidinium ion, and An$^-$ is a 1/p equivalent of a p-valent anion.

The compounds of formula (I) can be prepared according to or in analogy to the procedures disclosed in WO2005/014605; WO2006/056541 and WO2006/074983.

DETAILED DESCRIPTION

The scope of the present invention encompasses all combinations of substituent definitions, parameters and illustrations set forth above and below, either in general or within areas of the listed examples or embodiments, with one another, i.e., also any combinations between the particular areas and areas listed.

Whenever used herein the terms "including", "e.g.", "such as" and "like" are meant in the sense of "including but without being limited to" or "for example without limitation", respectively.

The term "polymer nanoparticles" denotes polymer nanoparticles comprising at least 50 wt.-%, for example, at least 80 wt.-%, or for example, at least 90 wt.-% of a polymer and having an average particle size of 1 to 10,000 nm, for example, 5 to 1,000 nm, or for example, 10 to 200 nm or 10 to 100 nm.

In an embodiment of the present invention, the term "polymer nanoparticles" denotes polymer nanoparticles consisting of a polymer having an average particle size as defined above.

The average particle size as used herein is defined as being the particle size (z average) measured using dynamic light scattering (DLS), which is also known as photon correlation spectroscopy (PSC) or quasi-elastic light scattering (QELS). The particle size measured thereby is also frequently called hydrodynamic diameter and reflects how a particle diffuses within a fluid. The measured hydrodynamic diameter is equivalent to that of an ideal sphere having the same translational diffusion coefficient as the particle being measured. Since the surface structure may have a significant influence, the hydrodynamic diameter measured using DLS can be significantly larger than the true diameter measured e.g. by electron microscopy.

In Dynamic Light Scattering (DLS), the polydispersity index (PDI) reflects the width of the particle size distribution. It ranges from 0 to 1. A value of zero refers to an ideal suspension with no distribution in size. Distributions with PDI values of 0.1 or smaller are called monodisperse while dispersions with values between 0.1 and 0.3 are considered as having a narrow size distribution. Dispersions having a PDI larger than 0.5 are considered being polydisperse.

Results referred to herein were obtained using a Zetasizer 3000 of Malvern Instruments, Malvern, UK with a fixed scattering angle of 90°.

To distinguish the particle size PDI obtained by DLS from the polydispersity index reflecting the molecular mass distribution of a polymer sample ($M_w/M_n$), the former is abbreviated as "DLS-PDI" and the latter as "M-PDI".

As used herein, and unless specifically stated otherwise, C$_6$-C$_{14}$-aryl denotes carbocyclic aromatic substituents, for example, phenyl, naphthyl, phenanthrenyl and anthracenyl, whereby said carbocyclic, aromatic substituents are unsubstituted or substituted by up to five identical or different substituents per cycle. For example, the substituents are selected from the group consisting of fluorine, bromine, chlorine, iodine, nitro, cyano, formyl or protected formyl, hydroxyl or protected hydroxyl, C$_1$-C$_8$-alkyl, C$_1$-C$_8$-haloalkyl, C$_1$-C$_8$-alkoxy, C$_1$-C$_8$-haloalkoxy, C$_6$-C$_{14}$-aryl, in particular phenyl and naphthyl, C$_7$-C$_{15}$-arylalkyl, in particular benzyl, di(C$_1$-C$_8$-alkyl)amino, (C$_1$-C$_8$-alkyl)amino, CO(C$_1$-C$_8$-alkyl), OCO(C$_1$-C$_8$-alkyl), NHCO(C$_1$-C$_8$-alkyl), N(C$_1$-C$_8$-alkyl)CO(C$_1$-C$_8$-alkyl), CO(C$_6$-C$_{14}$-aryl), OCO(C$_6$-C$_{14}$-aryl), NHCO(C$_6$-C$_{14}$-aryl), N(C$_1$-C$_8$-alkyl)CO(C$_6$-C$_{14}$-aryl), COO—(C$_1$-C$_8$-alkyl), COO—(C$_6$-C$_{14}$-aryl), CON($C_1$-$C_8$-alkyl)$_2$ or CONH($C_1$-$C_8$-alkyl), $CO_2M$, $CONH_2$, $SO_2NH_2$, $SO_2N(C_1$-$C_8$-alkyl)$_2$, $SO_3M$ and $PO_3M_2$.

In an embodiment of the present invention, the carbocyclic, aromatic substituents can be unsubstituted or substituted by up to three identical or different substituents per cycle selected from the group consisting of fluorine, chlorine, cyano, $C_1$-$C_8$-alkyl, $C_1$-$C_8$-haloalkyl, $C_1$-$C_8$-alkoxy, $C_1$-$C_8$-haloalkoxy, $C_6$-$C_{14}$-aryl, in particular phenyl.

In an embodiment of the present invention, the carbocyclic, aromatic substituents can be unsubstituted or substituted by up to three identical or different substituents per cycle selected from the group consisting of fluorine, $C_1$-$C_8$-alkyl, $C_1$-$C_8$-perfluoroalkyl, $C_1$-$C_8$-alkoxy, $C_1$-$C_8$-perfluoroalkoxy, and phenyl.

The definitions given above including the areas set forth as examples also apply analogously to the aryl moiety of a $C_7$-$C_{20}$-arylalkyl substituent.

As used herein and unless specifically stated otherwise, heterocyclyl denotes heterocyclic aliphatic, aromatic or mixed aliphatic and aromatic substituents in which no, one, two or three skeleton atoms per cycle, but at least one skeleton atom in the entire cyclic system is a heteroatom selected from the group consisting of nitrogen, sulphur and oxygen which are unsubstituted or substituted by up to five identical or different substituents per cycle, whereby the substituents are selected from the same group as given above for carbocyclic aromatic substituents including the areas set forth as examples.

In an embodiment of the present invention, heterocyclyl-substituents can, for example, include pyridinyl, oxazolyl, thiophen-yl, benzofuranyl, benzothiophen-yl, dibenzofuranyl, dibenzothiophenyl, furanyl, indolyl, pyridazinyl, pyrazinyl, imidazolyl, pyrimidinyl and quinolinyl, either unsubstituted or substituted with up to three substituents selected from the group consisting of fluorine, $C_1$-$C_8$-alkyl, $C_1$-$C_8$-perfluoroalkyl, $C_1$-$C_8$-alkoxy, $C_1$-$C_8$-perfluoroalkoxy, and phenyl.

The definitions given above, including the areas set forth as examples, also apply analogously to heterocyclylium cations, the bivalent heterocyclo-diyl substituents and the bivalent heterocyclo-diylium cations.

In an embodiment of the present invention, heterocyclylium cations can include, for example, N—($C_1$-$C_8$-alkyl) imidazolium or pyridinium cations.

In an embodiment of the present invention, heterocyclo-diylium cations can, for example, include N,N-imidazoldiylium cations.

As used herein, and unless specifically stated otherwise, protected formyl is a formyl substituent which is protected by conversion to an aminal, acetal or a mixed aminal acetal, whereby the aminals, acetals and mixed aminal acetals are either acyclic or cyclic.

In an embodiment of the present invention, protected formyl can include, for example, 1,1-(2,4-dioxycyclopentanediyl).

As used herein, and unless specifically stated otherwise, protected hydroxyl is a hydroxyl radical which is protected by conversion to a ketal, acetal or a mixed aminal acetal, whereby the aminals, acetals and mixed aminal acetals are either acyclic or cyclic. A specific example of protected hydroxyl is tetrahydropyranyl (O-THP).

As used herein, and unless specifically stated otherwise, $C_1$-$C_{18}$-alkyl, $C_1$-$C_{18}$-alkanediyl, $C_1$-$C_{18}$-alkoxy, $C_2$-$C_{18}$-alkenyl, $C_2$-$C_{18}$-alkenediyl and $C_1$-$C_{18}$-alkinediyl are a straight-chain, cyclic either in part or as a whole, branched or unbranched $C_1$-$C_{18}$-alkyl, $C_1$-$C_{18}$-alkanediyl, $C_1$-$C_{18}$-alkoxy, $C_2$-$C_{18}$-alkenyl, $C_2$-$C_{18}$-alkenediyl and $C_1$-$C_{18}$-alkinediyl substituents. The same applies to the alkandiyl moiety of an $C_7$-$C_{20}$-arylalkyl substituent.

Specific examples of $C_1$-$C_4$-alkyl include methyl, ethyl, n-propyl, isopropyl, n-butyl, tert-butyl. Additional examples for $C_1$-$C_8$-alkyl include n-pentyl, cyclohexyl, n-hexyl, n-heptyl, n-octyl, isooctyl. Additional examples for $C_1$-$C_8$-alkyl include $C_1$-$C_8$-alkyl norbornyl, adamantyl, n-decyl, n-dodecyl alkyl, n-hexadecyl, n-octadecyl.

Specific examples of $C_1$-$C_8$-alkanediyl-substituents include methylene, 1,1-ethylene, 1,2-ethylene, 1,1-propylene, 1,2-propylene, 1,3-propylene, 1,1-butylene, 1,2-butylene, 2,3-butylene and 1,4-butylene, 1,5-pentylene, 1,6-hexylene, 1,1-cyclohexylene, 1,4-cyclohexylene, 1,2-cyclohexylene and 1,8-octylene.

Specific examples of $C_1$-$C_4$-alkoxy-substituents include methoxy, ethoxy, isopropoxy, n-propoxy, n-butoxy and tert-butoxy. An additional example for $C_1$-$C_8$-alkoxy is cyclohexyloxy.

Specific examples of $C_2$-$C_8$-alkenyl- substituents include allyl, 3-propenyl and buten-2-yl.

As used hereinabove, $C_1$-$C_8$-haloalkyl and $C_1$-$C_8$-haloalkoxy are $C_1$-$C_8$-alkyl and $C_1$-$C_8$-alkoxy substituents which are once, more than once or fully substituted by halogen atoms. Substituents which are fully substituted by fluorine are referred to as $C_1$-$C_8$-perfluoroalkyl and $C_1$-$C_8$-perfluoroalkoxy, respectively.

Specific examples of $C_1$-$C_8$-haloalkyl-substituents are trifluoromethyl, 2,2,2-trifluoroethyl, chloromethyl, fluoromethyl, bromomethyl, 2-bromoethyl, 2-chloroethyl, nonafluorobutyl and n-perfluorooctyl.

In step A), an emulsion is prepared, whereby the emulsion comprises at least one surfactant, a dispersed phase and a continuous phase, whereby the dispersed phase comprises one or more polymerizable monomers and the continuous phase comprises water and one or more photoinitiators.

The preparation of the emulsion is typically effected by simply mixing the components and introducing mixing energy e.g. by standard agitators and/or static mixing elements, whereby the latter are particularly useful in flow-through reactors. Even though not typically necessary, the mixing can be supported by using high force dispersion devices such as, for example, ultrasound sonotrodes or high pressure homogenizers.

Step A), the preparation of the emulsion or step B) the polymerization or both steps A) and B) may either be performed batchwise or continuously.

The continuous phase comprises water and at least one photoinitiator and may further comprise water miscible solvents.

As used herein, the term water miscible organic solvent denotes organic solvents which are miscible with water in any ratio.

Suitable water miscible organic solvents include aliphatic alcohols, glycols, ethers, glycol ethers, pyrrolidines, N-alkylpyrrolidinones, N-alkyl pyrrolidones, polyethylene glycols, polypropylene glycols, amides, carboxylic acids, esters, sulfoxides, sulfones, hydroxyether derivatives such as butyl carbitol or cellosolve, amino alcohols, ketones, and the like, as well as derivatives thereof and mixtures thereof, provided, however, that they are miscible with water in any ratio.

Specific examples include methanol, ethanol, propanol, dioxane, ethylene glycol, propylene glycol, diethylene glycol, glycerol, dipropylene glycol or mixtures thereof.

The addition of water miscible organic solvents might be useful in those cases where the used amount of photoinitiator is either insoluble or incompletely soluble in water or the water-surfactant mixture.

In an embodiment of the present invention, the solubility of hydrophobic polymerizable monomers within the aqueous continuous phase can be typically raised so that the reaction rate, the particle size and the average molecular weight can be influenced by the added amount of water miscible organic solvent.

In an embodiment of the present invention, the addition of water miscible organic solvents allows the reaction temperature to be lowered significantly below the freezing point of water or the water-surfactant mixture.

In an embodiment of the present invention, the continuous phase comprises less than 20 wt-% of water-miscible organic solvents, for example, less than 10 wt-%, for example, less than 5 wt-% or less than 2 wt.-%. In an aspect of the present invention, the continuous phase does not contain water-miscible organic solvents.

In an embodiment of the present invention, the solubility of hydrophilic polymerizable monomers within the aqueous continuous phase can, for example, optionally be lowered by adding soluble salts such as inorganic salts like sodium chloride and the like. The content of inorganic salts may then be, for example, 0,1 to 5 wt.-%, or, for example, 0,1 to 1 wt.-%.

In an embodiment of the present invention, one or more photoinitiators of formula (I) can be used, where in formula (I):
n is 1,
m is 2,
$R^1$ is $C_6$-$C_{14}$-aryl or heterocyclyl or
  is $C_1$-$C_{18}$-alkyl, $C_2$-$C_{18}$-alkenyl, $C_7$-$C_{15}$-arylalkyl,
    which is either not or once, twice or more than twice interrupted by non-successive functional groups selected from the group consisting of:
      —O—, —$NR^4$—, —$N^+(R^4)_2An^-$—, —CO—, —OCO—, $NR^4(CO)$—, —(CO)$NR^4$—,
    and which is not, additionally or alternatively either once, twice or more than twice substituted by substituents selected from the group consisting of:
      halogen, cyano, epoxy, $C_6$-$C_{14}$-aryl; $C_1$-$C_8$-alkyl, $C_1$-$C_8$-alkoxy, $C_2$-$C_8$-alkenyl, $C_4$-$C_{15}$-arylalkyl, hydroxy, —$SO_3M$, —COOM, $PO_3M_2$, —$PO(N(R^5)_2)_2$, —$SO_2N(R^4)_2$, —$N(R^4)_2$, —$N^+(R^4)_3An^-$, heterocyclo-diylium$^+An^-$, —$CO_2N(R^5)_2$, —$COR^4$, —$OCOR^4$, $NR^4(CO)R^5$,
$R^2$ is $C_6$-$C_{14}$-aryl or heterocyclyl or
  is $C_1$-$C_8$-alkyl, $C_2$-$C_{18}$-alkenyl, $C_7$-$C_{15}$-arylalkyl,
    which is either not, once, twice or more than twice interrupted by non-successive functional groups selected from the group consisting of:
      —O—, —$NR^4$—, —$N^+(R^4)_2An^-$—, —CO—, $NR^4(CO)$—, —$NR^4(CO)O$—, (CO)$NR^4$—,
    and which is not, additionally or alternatively either once, twice or more than twice substituted by substituents selected from the group consisting of:
      halogen, cyano, $C_6$-$C_{14}$-aryl; heterocyclyl, $C_1$-$C_8$-alkyl, $C_1$-$C_8$-alkoxy, $C_1$-$C_8$-alkylthio, $C_2$-$C_8$-alkenyl, $C_4$-$C_{15}$-arylalkyl, —COOM, $SO_2N(R^3)_2$—, $N(R^4)_2$—, —$N^+(R^4)_3An^-$, —$CO_2N(R^4)_2$,
  whereby
$R^4$ is independently selected from the group consisting hydrogen, $C_1$-$C_8$-alkyl, $C_6$-$C_{14}$-aryl, $C_7$-$C_{15}$-arylalkyl and heterocyclyl or $N(R^4)_2$ as a whole is a N-containing heterocycle or $N^+(R^4)_2An^-$ and $N^+(R^4)_3An^-$ as a whole is or contains a cationic N-containing heterocycle with a counteranion,
$R^5$ is independently selected from the group consisting $C_1$-$C_8$-alkyl, $C_6$-$C_{14}$-aryl, $C_7$-$C_{15}$-arylalkyl and heterocyclyl or $N(R^5)_2$ as a whole is a N-containing heterocycle or $N^+(R^5)_2An^-$ and $N^+(R^5)_3An^-$ as a whole is or contains a cationic N-containing heterocycle with a counteranion,
M is hydrogen, lithium, sodium, potassium, one half equivalent of calcium, zinc or iron (II), or one third equivalent of aluminium (III) or is an ammonium ion or a primary, secondary, tertiary or quatenary organic ammonium ion, and
$An^-$ is 1/p equivalent of an p-valent anion.

In an embodiment of the present invention, one or more photoinitiators of formula (I) can be used, where in formula (I):
n is 1,
m is 2,
$R^1$ is $C_1$-$C_{18}$-alkyl, $C_2$-$C_{18}$-alkenyl, $C_7$-$C_{20}$-arylalkyl,
  which is either not or once, twice or more than twice interrupted by non-successive functional groups selected from the group consisting of:
    —O—, —$NR^4$—, —$N^+(R^4)_2An^-$—, —$NR^4(CO)$—, —(CO)$NR^4$—,
  and which is not, additionally or alternatively either once, twice or more than twice substituted by substituents selected from the group consisting of:
    halogen, $C_6$-$C_{14}$-aryl; $C_1$-$C_8$-alkyl, $C_1$-$C_8$-alkoxy, $C_2$-$C_8$-alkenyl, hydroxy, —$SO_3M$, —COOM, $PO_3M_2$, —$PO(N(R^5)_2)_2$, —$SO_2N(R^4)_2$, —$N(R^4)_2$, —$N^+(R^4)_3An^-$, heterocyclo-diylium$^+An^-$, —$CO_2N(R^5)_2$,
$R^2$ is $C_6$-$C_{14}$-aryl,
whereby
$R^4$ is independently selected from the group consisting hydrogen, $C_1$-$C_8$-alkyl, $C_6$-$C_{14}$-aryl, $C_7$-$C_{15}$-arylalkyl and heterocyclyl or $N(R^4)_2$ as a whole is a N-containing heterocycle or $N^+(R^4)_2An^-$ and $N^+(R^4)_3An^-$ as a whole is or contains a cationic N-containing heterocycle with a counteranion,
$R^5$ is independently selected from the group consisting $C_1$-$C_8$-alkyl, $C_6$-$C_{14}$-aryl, $C_7$-$C_{15}$-arylalkyl and heterocyclyl or where $N(R^5)_2$ as a whole is a N-containing heterocycle or $N^+(R^5)_2An^-$ and $N^+(R^5)_3An^-$ as a whole is or contains a cationic N-containing heterocycle with a counteranion,
M is hydrogen, lithium, sodium, potassium, one half equivalent of calcium, zinc or iron (II), or one third equivalent of aluminium (III) or is an ammonium ion or a primary, secondary, tertiary or quatenary organic ammonium ion, and
$An^-$ is 1/p equivalent of a p-valent anion, preferably a halide, a carboxylate, $C_1$-$C_8$-alkylsulfate, $C_6$-$C_{14}$-arylsulfate, hexafluorophoaphate, tetrafluoroborate, dihydrogenphosphate, one half equivalent of sulphate or hydrogenphosphate.

In an embodiment of the present invention, one or more photoinitiators of formula (I) can be used, where in formula (I):
n is 1,
m is 2,
$R^1$ is $C_1$-$C_8$-alkyl,
  which is either not or once, twice or more than twice interrupted by non-successive functional groups selected from the group consisting of:

—O—, —NR⁴—, —N⁺(R⁴)₂An⁻—,
and which is not, additionally or alternatively either once, twice or more than twice substituted by substituents selected from the group consisting of:
halogen, $C_1$-$C_8$-alkoxy, hydroxy, —SO₃M, —COOM, PO₃M₂, SO₂N(R⁴)₂, —N(R⁴)₂, —N⁺(R⁴)₃An⁻, —CO₂N(R⁴)₂, $C_1$-$C_8$-alkylsulfate, R² is $C_6$-$C_{14}$-aryl, whereby R⁴ is independently selected from the group consisting hydrogen, $C_1$-$C_8$-alkyl, $C_6$-$C_{14}$-aryl, $C_7$-$C_{15}$-arylalkyl and heterocyclyl or N(R⁴)₂ as a whole is a N-containing heterocycle or N⁺(R⁴)₂An⁻ and N⁺(R⁴)₃An⁻ as a whole is or contains a cationic N-containing heterocycle with a counteranion, M is hydrogen, lithium, sodium, potassium, one half equivalent of calcium, zinc or iron (II), or one third equivalent of aluminium (III) or is an ammonium ion or a primary, secondary, tertiary or quatenary organic ammonium ion, and An⁻ is 1/p equivalent of an p-valent anion, for example, a halide, a carboxylate, $C_1$-$C_8$-alkylsulfate, $C_6$-$C_{14}$-arylsulfate, hexafluorophoaphate, tetrafluoroborate, dihydrogenphosphate, one half equivalent of sulphate or hydrogenphosphate.

In an embodiment of the present invention, one or more photoinitiators of formula (I) can be used, where in formula (I):

n is 1,
m is 2,
R¹ is $C_1$-$C_8$-alkyl,
which is either not or once, twice or more than twice interrupted by non-successive functional groups selected from the group consisting of:
—O—, —NR⁴—, —N⁺(R⁴)₂An⁻—, for example, those containing one to ten polyethyleneglycolether groups [—OCH₂CH₂]ₓ—,
and which additionally or alternatively are either once, twice or more than twice substituted by substituents selected from the group consisting of:
hydroxy, —SO₃M, —COOM, PO₃M₂, —N(R⁴)₂, —N⁺(R⁴)₃An⁻, heterocyclylium⁺An⁻, R² is $C_6$-$C_{14}$-aryl, for example, mesityl or 2,6-dimethoxyphenyl, whereby R⁴ is independently selected from the group consisting hydrogen, $C_1$-$C_8$-alkyl, $C_6$-$C_{14}$-aryl, $C_7$-$C_{15}$-arylalkyl and heterocyclyl or N(R⁴)₂ as a whole is a N-containing heterocycle or N⁺(R⁴)₂An⁻ and N⁺(R⁴)₃An⁻ as a whole is or contains a cationic N-containing heterocycle with a counteranion, M is hydrogen, lithium, sodium, potassium, one half equivalent of calcium or zinc or is an ammonium ion or a primary, secondary, tertiary or quatenary organic ammonium ion, and An⁻ is 1/p equivalent of a p-valent anion, for example, a halide, a carboxylate, $C_1$-$C_8$-alkylsulfate, $C_6$-$C_{14}$-arylsulfate, hexafluorophoaphate, tetrafluoroborate, dihydrogenphosphate, one half equivalent of sulphate or hydrogenphosphate.

Particularly suitable for the process according to the present invention are water-soluble photoinitiators. Some of the aforementioned photoinitiators of formula (I) are novel.

An aspect of the present invention provides photoinitiators of formula (Ia):

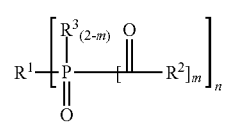

(Ia)

wherein n, m, R¹ to R⁵ and An have the meaning given above including the areas listed as examples, provided, however, that the molecule contains at least one functional group or substituent selected from the group consisting of:
—SO₃M, —COOM, PO₃M₂, —N⁺(R⁴)₃An⁻, heterocyclylium⁺An⁻.

wherein

M is 1/q equivalent of an q-valent metal ion or is an ammonium ion or a primary, secondary, tertiary or quatenary organic ammonium ion or a guanidinium ion.

In an embodiment of the present invention, photoinitiators of formula (Ia) can, for example, be those where in formula (Ia):

n is 1,
m is 2,
R¹ is $C_1$-$C_8$-alkyl which is either once, twice or more than twice substituted by substituents selected from the group consisting of:
—SO₃M, —COOM, PO₃M₂, —N⁺(R⁴)₃An⁻ and heterocyclylium⁺An⁻, and R² is mesityl or 2,6-dimethoxyphenyl, whereby R⁴ is independently selected from the group consisting of hydrogen and $C_1$-$C_8$-alkyl, M is lithium, sodium or potassium, or is an ammonium ion or a primary, secondary, tertiary or quatenary organic ammonium ion, and An⁻ is a halide, a carboxylate, a $C_1$-$C_8$-alkylsulfate, a $C_6$-$C_{14}$-arylsulfate, hexafluorophoaphate, tetrafluoroborate, dihydrogenphosphate or one half equivalent of sulphate or hydrogenphosphate.

The compounds of formula (Ia) can be prepared analogous to the procedures described in WO2005/014605; WO2006/056541 and WO2006/074983.

In an embodiment of the present invention, the compounds of formula (Ia) can, for example, be prepared by the steps of:

A) contacting elemental phosphorous with a alkali or alkaline earth metal optionally in the presence of a catalyst or an activator in a solvent to obtain metal phosphides M₃P, wherein M is an alkali or alkaline earth metal or to obtain alkali metal polyphosphides or alkaline earth metal polyphosphides;

B) optionally adding a proton source, optionally in the presence of a catalyst or an activator to obtain metal dihydrogen phosphides MPH₂ which may depending on the proton source exist as complexes;

C) acylating with:
two equivalents of acid halides of formula (III)

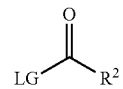

(III)

to obtain compounds of formula (IV)

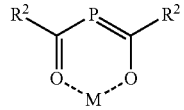

or with one equivalent of acid halides of formula (III) and one compound of formula (V)

LG-R³ (V)

to obtain compounds of formula (VI)

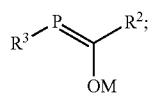

D) alkylation reaction with an electrophilic agent such as those of formula (VIIa or VIIb)

LG-R¹ (VIIa)

LG-R¹''-LG (VIIb)

to obtain compounds of formula (VIII)

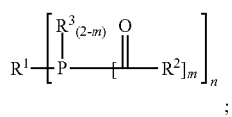

and

E) oxidation of compounds of formula (VIII) to compounds of formula (Ia), whereby in formulae (III), (IV), (V), (VI), (VIIa), (VIIb), (VIII) and (Ia)

n, m, $R^1$ to $R^3$ have the same meaning and example areas as given above for formula (Ia) and LG denotes a leaving group, for example, chlorine, bromine or iodine or $C_1$-$C_8$-alkylsulfonyloxy.

In the context of the present invention, formula (VI) can also include isomers of formula (VIa):

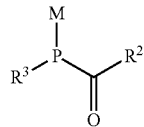

The oxidation according to step E) can be performed in an usual manner known in the art e.g. by using oxygen, sodium hypochlorite, hydrogenperoxide or organic peroxides.

Compounds of formula (I) or (Ia), wherein $R^1$ is $C_1$-$C_{18}$-alkoxy or —N($R^4$)$_2$ may be prepared for example by F) reacting compounds of formulae (IV) or (VI) optionally after protonation with halogens or interhalogen compounds or halogen releasing compounds to obtain compounds of formula (VIIIa)

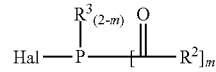

and reacting the compounds of formula (VIIIa) with compounds of formulae (IXa) or (IXb)

H—R wherein R is $C_1$-$C_{18}$-alkoxy or —N($R^4$)$_2$ optionally in the presence of a base whereby $R^2$ to $R^{4'}$ n and m have the same meaning and example areas as given above for formula (Ia) and Hal is Halogen, for example, chlorine, bromine or iodine.

Halogen releasing compounds include e.g. hexachloroethane.

In an embodiment of the present invention, steps F) and G) can be performed simultaneously.

For some of the substitution patterns mentioned above, standard protection and deprotection techniques might have to be applied in order to enhance the chemicals yield of the compounds.

The compounds of formula (Ia) may be further functionalized by standard operations such as alkylations, nucleophilic substitutions, protonations with acids, deprotonations with bases, optionally followed by ion exchange and the like in order to obtain other compounds of formula (Ia).

Further details are given in the examples.

The compounds of formulae (VIII) and (VIIIa) are also an aspect of the present invention.

The emulsion further contains one or more polymerizable monomers.

As used herein, the term polymerizable monomer encompasses all monomers which can be polymerized in a radical polymerization.

Polymerizable monomers can, for example, be those of formula (II):

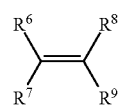

wherein $R^6$, $R^7$, $R^8$ and $R^9$ are independently of one another selected from the group consisting of:

$C_1$-$C_{18}$-alkoxy, $C_1$-$C_{18}$-alkyl, $C_2$-$C_{18}$-alkenyl, $C_7$-$C_{15}$-arylalkyl which is either not, once, twice or more than twice interrupted by non-successive functional groups selected from the group consisting of:

—O—, —CO—, —OCO—, —O(CO)O—, NR⁴(CO)—, —NR⁴(CO)O—, —O(CO)NR⁴—, —(CO)NR⁴—, —NR⁴(CO)NR⁴—, —Si($R^5$)$_2$—, —OSi($R^5$)$_2$—, —OSi($R^5$)$_2$O—, —Si($R^5$)$_2$O— and which is either not, once, twice or more than twice interrupted by bivalent residues selected from the group consisting of heterocyclo-diyl and $C_6$-$C_{14}$-aryldiyl, and which is not, additionally or alternatively either once, twice or more than twice substituted by substituents selected from the group consisting of:

halogen, cyano, epoxy, $C_6$-$C_{14}$-aryl; heterocyclyl, $C_1$-$C_8$-alkyl, $C_1$-$C_8$-alkoxy, $C_1$-$C_8$-alkylthio, $C_2$-$C_8$-alkenyl, $C_4$-$C_{15}$-arylalkyl, hydroxy, —$SO_2N(R^4)_2$, $NR^4SO_2$—$R^5$, —$N(R^4)_2$, —$CO_2N(R^5)_2$, —$COR^4$, —$OCOR^4$, —$O(CO)OR^4$, $NR^4(CO)R^5$, —$NR^4(CO)OR^5$, $O(CO)N(R^4)_2$, —$NR^4(CO)N(R^4)_2$, —$OSi(OR^5)_{y-3}(R^5)_y$, —$Si(OR^5)_{y-3}(R^5)_3$, where y is 1, 2 or 3.

Examples of polymerizable monomers include:

Mono(meth)acrylates, such as methyl-, ethyl-, butyl-, 2-ethylhexyl- and 2-hydroxyethyl acrylate, isobornyl acrylate gl;

other unsaturated carboxylic acid esters such as $C_1$-$C_8$-alkylesters of crotonic acid, maleic acid, fumaric acid, itaconic acid, cinnamic acid and unsaturated fatty acids such as linolenic acid or oleic acid.ycidylacrylate, glycidylmethacrylate and methyl and ethyl methacrylate, acrylnitrile;

poly(meth)acrylates such as ethylene glycol diacrylate, 1,6-hexanediol diacrylate, propylene glycol diacrylate, dipropylene glycol diacrylate, tripropylene glycol diacrylate, neopentyl glycol diacrylate, hexamethylene glycol diacrylate and bis-phenol-A diacrylate, 4,4'-bis(2-acryloyloxyethoxy)diphenylpropane, trimethylolpropane tri-acrylate, pentaerythritol triacrylate, pentaerythritol tetraacrylate, vinyl acrylate, divinylbenzene, divinyl succinate, diallyl phthalate, triallyl phosphate, triallyl isocyanurate, tris-(hydroxyethyl) isocyanurate triacrylate (Sartomer 368; from Cray Valley) and tris(2-acryloyl-ethyl) isocyanurate, ethyleneglycoldivinylether, diethyleneglycoldivinylether, triethylene-glycoldivinylether, polyethyleneglycol-mono-(meth)acrylate, polyethylene-glycol-di-(meth) acrylate;

other crosslinking olefins such as divinyl-benzene;

vinyl esters, such as vinyl acetate;

vinyl ethers, such as isobutyl vinyl ether;

styrenes such as styrene and styrene substituted by $C_1$-$C_8$-alkyl- or halogen or sulfonic acid salts at the aromatic ring;

siloxanes such as trimethoxyvinylsilane, triethoxyvinylsilane; and monoalkenes and polyalkenes like isobutene, butadiene, isoprene.

More polymerizable monomers are styrene, para-methylstyrene, sodium 4-vinyl-benzosulfonate, butylmethacrylate, butylacrylate, acrylnitrile, glycidylacrylate, and glycidylmethacrylate or mixtures thereof.

In an embodiment of the present invention, the polymerizable monomer or the mixture of polymerizable monomers can be used in an amount that the content of the polymerizable monomer or the mixture of polymerizable monomers in the continuous phase is less than 50 g/l, for example, less than 25 g/l, or for example, less than 10 g/1 or less than 2 g/l.

In an embodiment of the present invention, the polymerizable monomer or the mixture of polymerizable monomers can be selected from those resulting in polymer nanoparticles having a glass transition temperature or a melting point or melting range higher than the polymerization temperature in order to avoid immediate agglomeration.

The weight ratio of photoinitiator to polymerizable monomer is typically between 1:5 and 1:100.000, for example, between 1:10 and 1:10.000 and for example, 1:50 to 1:1,000.

In step A), the photoinitiator may be either added completely or partially. If in step A) the photoinitiator is added partially, the rest can be added during step B) either batchwise or continuously.

The emulsion further comprises at least one surfactant. Suitable surfactants are, for example, non-ionic, cationic or anionic or amphoteric surfactants.

Surfactants can, for example, be anionic surfactants such as $C_6$-$C_{24}$-alkyl sulfonates, $C_6$-$C_{24}$-perfluoroalkyl sulfonates $C_6$-$C_{24}$-alkyl ether sulfonates, $C_7$-$C_{24}$-aryl alkyl sulfonates, $C_6$-$C_{24}$-alkyl aryl sulfonates, $C_1$-$C_{24}$-alkyl succinates, $C_1$-$C_{24}$-alkyl sulfo succinates, N—($C_1$-$C_{24}$-alkyl)-sarkosinate, acyltaurates, $C_6$-$C_{24}$-perfluoroalkyl carboxylates, $C_6$-$C_{24}$-alkyl phosphates, $C_6$-$C_{24}$-alkyl ether phosphates, $C_6$-$C_{24}$-alkyl ether carboxylates, in particular the alkali metal, ammonium-, and organic ammonium salts of the aforementioned compounds and cationic surfactants such as quatenary ammonium salts or pyridinium salts.

In an embodiment of the present invention, at least one surfactant can be selected from the group consisting of sodium lauryl sulfonate, ammonium lauryl sulfonate, sodium lauryl ether sulfonate, ammonium lauryl ether sulfonate, sodium lauryl sarkosinate, sodium oleyl succinate, sodium dodecylbenzene sulfonate, triethanolamine dodecyl benzene sulphate, cetyltrimethylammonium bromide, cetylpyridinium chloride, polyethoxylated tallow amine, benzalkonium chloride and benzethonium chloride.

The weight ratio of surfactant and the continuous phase is typically between 1:10.000 and 1:10, for example, between 1:1.000 and 1:50, whereby the amount should be at least equal or higher than the critical micelle concentration (CMC) in the emulsion. The CMC is defined as being the lowest concentration of surfactant at which micelle formation is observed and which is dependent on the nature of the surfactant used.

The weight ratio of the aqueous continuous phase and the dispersed phase depends on the surface energy and the phase inversion point but is typically between 1:2 and 500:1, for example, between 1.5:1 and 20:1.

In step B), the emulsion of step A) is exposed to electromagnetic radiation having a wavelength sufficient to induce the generation of radicals from the photoinitiator.

Upon exposure to said electromagnetic radiation, the photoinitiator molecules typically undergo exitation to the singlet state, electron-spin reversal to the triplet state and defragmentation thereby forming at least two radicals. At least some of these radicals are capable of initiating a radical polymerization of the polymerizable monomers.

For the photoinitiators according to formula I, the radical formation is typically induced by exposure to electromagnetic radiation having a wavelength of below 500 nm, for example, below 450 nm, for example, in the range of 200 to 450 nm, such as in the range of 300 to 440 nm.

As a consequence, suitable sources of electromagnetic radiation having a wavelength sufficient to induce the generation of radicals from the photoinitiator include eximer lasers such as KrF and XeF-lasers; UV lamps like medium-pressure, super-high-pressure, high-pressure and low-pressure mercury lamps which can be undoped or doped e.g. with gallium iodide, thallium iodide or other metal halides; blue or white LEDs; concentrated, direct or indirect sunlight; xenon or xenon mercury arc lamps such as continuous-output xenon short- or long-arc lamps, xenon or xenon mercury flash lamps or other flash lamps; microwave-excited metal vapour lamps; excimer lamps, superactinic fluorescent tubes; fluorescent lamps; and noble gas incandescent lamps.

The determination of a suitable reaction temperature range during polymerization depends on the composition of the aqueous continuous phase, the composition of the dispersed phase and the reaction pressure since freezing or boiling in the emulsion should be avoided.

In an embodiment of the present invention, the polymerization according to step B) can, for example, be carried out at a temperature range of from −30° C. to 120° C., for example, from −10 to 80° C. and for example, from 0 to 40° C.

In an embodiment of the present invention, the polymerization according to step B) can, for example, be carried out at a pressure range of from 100 hPa to 10 Mpa, for example, from 500 hPa to 1 MPa and for example, from 800 hPa to 1.2 MPa. The reaction can, for example, be carried out under ambient pressure.

The pH value of the aqueous continuous phase is typically in the range of 3 to 10, for example, in the range of 5 to 9 calculated on standard conditions. If compounds of formula (I) are used which bear carboxylic acid groups, a pH value above the pKa value of the respective compound of formula (I) can, for example, be used.

The exposure to electromagnetic radiation depends on the intensity but typically can, for example, last for is to 24 h, for example, for 10 s to 3 h.

In an embodiment of the present invention, the amount of electromagnetic radiation having a wavelength sufficient to induce the generation of radicals can be from 10 J/1 to 500 kJ/1 of the emulsion, for example, 100 J/1 to 50 kJ/1.

After the exposure to electromagnetic radiation, the reaction might either continue or not, depending on the remaining polymerizable monomers in the emulsion. In those cases where the polymerization is not finished after the exposure to electromagnetic radiation ends, the reaction mixture is either reacted further e.g. for 1 min to 10 h or terminated immediately of after e.g. 1 min to 10 h by adding radical scavengers such as hydroquinones, diphenyldisulfides, phenothiazine and the like.

In an embodiment of the present invention, the polymerization can be terminated after consumption of 60 to 99 wt-% of the polymerizable monomers, for example, after consumption of 65 to 90 wt.-%.

In an embodiment of the present invention, the residual polymerizable monomers can be removed from the resulting dispersion by standard stripping or distillation techniques.

In an embodiment of the present invention, the process can be carried out using a batch reactor or a flow-through reactor, whereby the reactors allow the irradiation of the emulsion contained therein with electromagnetic radiation.

The polymer nanoparticles are obtained via the process according to the present invention as an aqueous suspension.

The main advantage of the process according to the present invention is that it allows the efficient synthesis of polymer particles in the nanometer to micrometer range. Unprecedented control over the dispersity of the size and the molecular weight distribution can be achieved. Furthermore, the molecular weight of the individual polymer chains is typically very high.

The polymer nanoparticles obtained typically have a M-PDI of 1.00 to 1.50, for example, a M-PDI of 1.02 to 1.40.

The polymer nanoparticles further typically have a DLS-PDI of 0.05 to 0.50, for example, a DLS-PDI of 0.10 to 0.30.

The molecular weight of the polymer chains within the polymer nanoparticles typically have a weight average molecular mass of more than 500 kg/mol to 5,000 kg/mol, for example, 1,000 kg/mol to 5,000 kg/mol.

Therefore, an embodiment of the present invention relates to polymer nanoparticles having a DLS-PDI of 0.05 to 0.50, for example, 0.10 to 0.30 and a M-PDI of 1.00 to 1.50, for example, 1.02 to 1.40 and/or a weight average molecular mass of more than 500 kg/mol to 5,000 kg/mol, for example, 1,000 kg/mol to 5,000 kg/mol.

In an embodiment of the present invention, polymer suspensions comprise 0,001 to 50 wt-%, for example, 0.001 to 25 wt-% and for example, 0.5 to 20 wt-% of the aforementioned polymer nanoparticles.

The polymer nanoparticles can be concentrated in or isolated from the dispersions using standard techniques well known to those skilled in the art. For example, inorganic salts or solutions thereof are added to the suspension and the resulting mixture can be subjected to centrifugation, sedimentation, filtration or other separation processes of a like nature.

In an embodiment of the present invention, the concentration or isolation can be performed by nano- or microfiltration using membranes.

In an embodiment of the present invention, the aforementioned polymer suspensions or polymer nanoparticles can be used, for example, in coating, adhesive, ink, and painting materials, precision mold constructions, in the manufacture of electronic articles, for drug delivery systems, diagnostic sensors and contrast agents.

An aspect of the present invention therefore provides coatings, adhesives, inks, and painting materials, precision mold constructions, electronic articles, drug delivery systems, diagnostic sensors and contrast agents comprising the polymer nanoparticles according to the present invention.

The present invention is further illustrated by the examples without being limited thereby.

EXAMPLES

I Preparation of Photoinitiators and their Precursor Materials

1) Preparation of sodium bis(mesitoyl)phosphide

In a 100 mL thick-walled Schlenk flask equipped with a teflon screw cap, sodium (1.73 g, 0.075 mmol, 3 eq.) and red phosphorus (0.78 g, 0.025 mmol, 1 eq.) were put together under inert conditions. A glass covered magnetic stirrer was added and 20 mL of ammonia were condensed into the flask, by cooling with dry ice/acetone to −78° C. Subsequently, dimethoxyethane (dme) (20 mL) was added and the flask was closed and warmed up to room temperature. After 90 min, stirring at room temperature a change in colour from blue to dark yellow was observed and after another 30 min, the colour became intensively yellow. The pressure in the reaction vessel was 7 to 8 bar. The reaction mixture was cooled down to −40° C. The Schlenk flask, which now had a pressure of 1 bar, was opened and tert-butanol (3.71 g, 0.05 mol, 2 eq.) was added. The reaction mixture was warmed up to room temperature over a period of two hours. Finally, the solvent was completely removed in vacuo at room temperature. The remaining oil was dissolved in dme (40 mL). Mesitoyl chloride (9.15 g, 0.05 mol, 2 eq.) was added dropwise.

i): Isolation of the product under dry conditions: The reaction mixture was stirred for one hour at room temperature, the precipitate of sodium chloride was removed by filtration and the solvent was evaporated in vacuo. The pure microcrystalline product can be obtained by dissolving the sodium bis(mesitoyl)phosphide in dme and precipitation with n-hexane (Yield: 5.89 g, 67.7%).

ii). Working up with degassed water: The reaction mixture was mixed with 100 mL degassed, distilled water. After stirring the solution until the sodium chloride was completely dissolved, the reaction mixture was extracted three times with 50 mL of toluene. After removing the toluene in vacuo, the pure product remained. It can contain small amounts of water, which can be completely removed by azeotropic distillation with toluene. The product was dissolved in toluene and the solvent was removed in vacuo afterwards again. This procedure was repeated two or three times. The yield was the same as for procedure a).

m.p.: 208° C. (Decomposition).

$^{31}$P NMR (101.25 MHz): δ=84.1 ppm (br.).

2) Preparation of sodium bis(2,6-dimethoxybenzoyl)phosphide

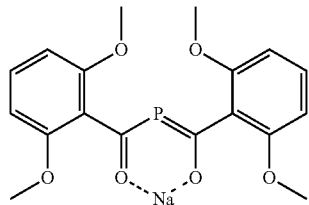

NaPH$_2$×2 NaO$^t$Bu (0.846 g, 3.41 mmol, 1 eq.) was dissolved in dme (6 mL) and cooled in an ice water bath to 0° C. 2,6-dimethoxybenzoyl chloride (1.37 g, 6.82 mmol, 2 eq.) dissolved in dme (8 mL) was added dropwise to the solution. After 1 hour of stirring at room temperature the solvent was removed in vacuo to yield a yellow powder of sodium bis(2,6-dimethoxy-benzoyl)phosphide (Yield: 87%, 1.14 g, 2.97 mmol).

$^{31}$P{$^1$H}-NMR (121.5 MHz, d$^8$-thf): δ=91.0 (s).

3) Preparation of ((2,3-dihydroxypropyl)phosphoryl)bis(mesitylmethanone)

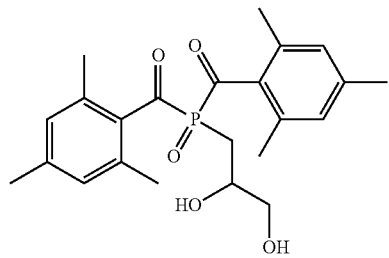

Sodium bis(mesitoyl)phosphide of example 1 (250 mg, 0.72 mmol, 1 eq.) was dissolved in thf (5 mL). 1-Bromo-2,3-propanediol (111.6 mg, 0.063 mL, 0.72 mmol, 1 eq.) was added and the solution was stirred overnight. The white precipitate was filtered off. The thf was removed in vacuo and the phosphane was dissolved in ethanol (5 mL). Hydrogen peroxide (10%) (0.244 mL, 0.72 mmol, 1 eq.) was added and the solution was stirred overnight. Diethyl ether (5 mL) was added and the solution was washed with sodium hydrogen carbonate solution (2%) and brine. After drying with sodium sulfate, the solvent was evaporated. A pale yellow product was obtained (Yield: 64%, 0.46 mmol, 191.5 mg).

$^{31}$P NMR (121.5 MHz, C$_6$D$_6$): δ=26.4 (t, J=16.8 Hz)

4) Preparation of ((3-bromopropyl)phosphinediyl)bis(mesitylmethanone)

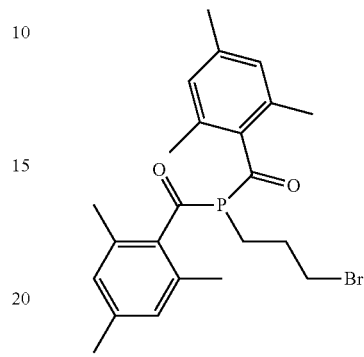

Sodium bis(mesitoyl)phosphide of example 1 (1.00 g, 2.88 mmol, 1 eq.) was dissolved in toluene (5.00 mL). This solution was added dropwise in a cooled (ice bath) solution of 1,3-dibromopropane (0.028 mL, 0.056 g, 28.8 mmol, 10 eq.) in thf (5.00 mL). Then the reaction mixture was stirred for 24 hours at 50° C. to complete the reaction. A white precipitate of sodium bromide was formed. After removing the sodium bromide by filtration, the solution was evaporated in vacuo. The remaining yellow oil was dissolved in diethyl ether and washed with an aqueous and degassed ammonium chloride solution (5%). After the ether solution was dried with sodium sulfate it was evaporated in vacuum at room temperature and dried in high vacuum for 4 hours to remove the excess of 1,3-dibromopropane. (Yield: 1.16 g, 2.59 mmol, 90%).

$^{31}$P NMR: (121.5 MHz, C$_6$D$_6$): δ=50.8 (t, J=9.6 Hz).

5) Preparation of ((3-bromopropyl)phosphoryl)bis(mesitylmethanone)

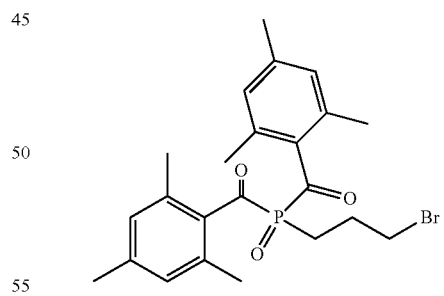

((3-bromopropyl)phosphinediyl)bis(mesitylmethanone) of example 4 (1.16 g, 2.59 mmol, 1 eq.) was dissolved in toluene (5 mL) and hydrogen peroxide (10%) (8.88 mL, 2.59 mmol, 1 eq.) was added. The reaction mixture was stirred at 40° C. for 12 hours. Afterwards diethylether (50 mL) were added and the solution was washed with twice sodium hydrogencarbonate (2%) solution, once with brine and finally dried with magnesium sulfate. After removing the solvent in vacuo at room temperature, the pure product was obtained as a yellow oil (Yield: 0.97 g, 2.10 mmol).

$^{31}$P NMR (121.5 MHz, C$_6$D$_6$): δ=25.83 (t, J=9.7 Hz).

6) Preparation of ((3-aminopropyl)phosphoryl)bis(mesitylmethanone)

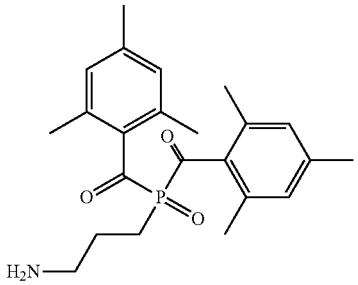 [SMILES: Cc1cc(C)c(C(=O)P(=O)(CCCN)C(=O)c2c(C)cc(C)cc2C)c(C)c1]

Sodium bis(mesitoyl)phosphide of example 1 (22.8 mg, 0.065 mmol, 1 eq.) was dissolved in dme (2 mL). 3-Bromopropylammonium bromide (14 mg, 0.065 mmol, 1 eq.) was added at room temperature. After 15 minutes of stirring, the solvent was removed in vacuo at room temperature and replaced by 2 mL ethanol. With a microlitre syringe hydrogen peroxide (30%) (0.008 ml, 0.065 mmol, 1 eq.) was added slowly. The solution was stirred for 30 minutes. Subsequently, the solvent was removed in vacuo. The product was dissolved in diethylether (2 mL), washed with brine and dried with sodium sulfate. After filtration and evaporation of the diethylether, the pure product was obtained (Yield not determined).

$^{31}P\{^1H\}$-NMR (121.5 MHz, $C_6D_6$): δ=23.1 (s).

7) Preparation of 3-(bis(2,6-dimethoxybenzoyl)phosphino)propylamine

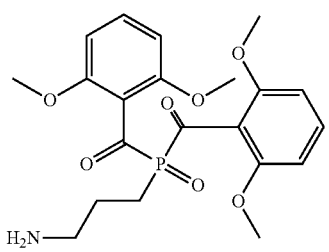 [SMILES: COc1cccc(OC)c1C(=O)P(=O)(CCCN)C(=O)c1c(OC)cccc1OC]

Sodium bis(2,6-dimethoxybenzoyl)phosphide of example 2 (25 mg (0.065 mmol, 1 eq.) was dissolved in dme (2 mL). 3-Bromopropylamine hydrobromide (14 mg, 0.065 mmol, 1 eq.) was added at room temperature. After stirring the reaction mixture for 15 minutes, the solvent was removed in vacuo at room temperature and replaced by ethanol (2 mL). With a microlitre syringe hydrogen peroxide (30%) (0.008 ml, 0.065 mmol, 1 eq.) was added slowly and the solution was stirred for 30 minutes. Subsequently, the solvent was removed in vacuo. The residue was dissolved in diethylether (2 mL) and washed with brine and dried with sodium sulfate. After filtration and evaporation of the diethylether the pure product was obtained.

$^{31}P\{^1H\}$ NMR (121.5 MHz, $d^8$-thf): δ=24.1 (s).

8) Preparation of 3-(3-(bis(2,4,6-trimethylbenzoyl)phosphoryl)propyl)-1-methyl-1H-imidazol-3-ium bromide

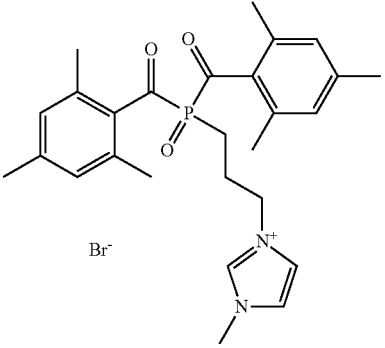

((3-Bromopropyl)-phosphoryl)bis(mesitylmethanone) of example 5 (825 mg, 1.78 mmol, 1 eq.) and methylimidazol (0.15 mL, 155 mg, 1.89 mmol, 1.06 eq.) were dissolved in toluene (2 mL). The solution was stirred for 24 h at 50° C. A yellow precipitate was formed. The solution was decanted and the yellow solid was washed three times with 2 mL toluene. The microcrystalline product was dried for two hours in vacuo.

$^{31}P$ NMR (101.25 MHz, $D_2O$): δ=23.1 (br.)

9) Preparation of bis(2,6-dimethoxybenzoyl)hydroxyethylphosphanoxide

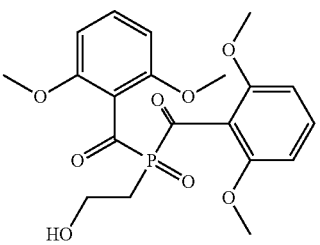 [SMILES: COc1cccc(OC)c1C(=O)P(=O)(CCO)C(=O)c1c(OC)cccc1OC]

Sodium bis(2,6-dimethoxybenzoyl)phosphide of example 2(25 mg, 0.065 mmol, 1 eq.) was dissolved in dme (2 mL). With a microlitre syringe 2-bromoethanol (0.005 ml, 0.065 mmol, 1 eq.) was added at room temperature. After stirring the reaction mixture for 15 minutes, the solvent was removed in vacuo at room temperature and replaced by ethanol (2 mL). To this solution hydrogen peroxide (30%) (0.008 ml, 0.065 mmol, 1 eq.) was added slowly with a microlitre syringe. The solution was stirred for 5 minutes. Subsequently, the solvent was removed in vacuo (Yield: 76%, 0.05 mmol, 20.85 mg).

$^{31}P$ NMR (101.3 MHz, $d^8$-thf): δ=26.47 (br.).

10) Preparation of 2-(bis(2,4,6-trimethylbenzoyl)phosphino)acetic acid

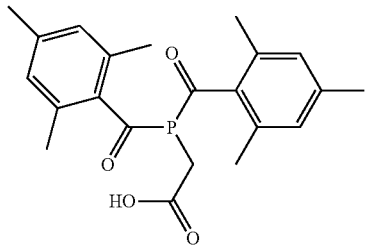

Sodium bis(mesitoyl)phosphide of example 1 (1.00 g, 2.88 mmol, 1 eq.) was dissolved in thf (5.00 mL). Bromoacetic acid (0.40 g, 2.88 mmol, 1 eq.) was dissolved in thf (5.00 mL). The solutions were mixed and stirred for 24 hours at room temperature. A white precipitate of sodium bromide was formed. After removing the sodium bromide by filtration, the solution was evaporated in vacuo. The remaining yellow oil was dissolved in diethyl ether and washed with an aqueous and degassed ammonium chloride solution (5%). After the ether solution was dried with sodium sulfate, the solvent was evaporated in vacuum at room temperature and dried in high vacuum for 4 hours. (Yield: 0.96 g, 2.51 mmol, 87%)

$^{31}$P NMR (101.3 MHz, C$_6$D$_6$): δ=46.7.

11) Preparation of 2-(bis(2,4,6-trimethylbenzoyl)phosphoryl)acetic acid (BAPO-acetic acid)

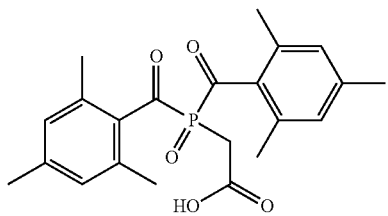

2-(Bis(2,4,6-trimethylbenzoyl)phosphino)-acetic acid of example 10 (1.00 g, 2.60 mmol, 1 eq.) was dissolved in degassed ethanol (5.00 mL) and hydrogen peroxide (30%) (0.29 mL, 2.60 mmol, 1 eq.) was added. The solution was stirred at 40° C. for one hour. The ethanol was removed in vacuo at room temperature. A white crystalline powder was obtained, which could easily be recrystallised from 40° C. warm water (Yield: Quantitative).

$^{31}$P NMR (121.5 MHz, C$_6$D$_6$): δ=19.6 (t, J=10.9 Hz).

12) Preparation of 2-(bis(2,6-dimethoxybenzoyl)phosphino)acetic acid ($^{MeO}$BAP acetic acid)

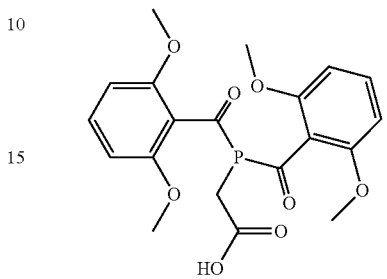

Sodium bis(2,6-dimethoxybenzoyl)phosphide of example 2 (100 mg, 0.26 mmol, 1 eq.) was dissolved in dme (5 mL), bromoacetic acid (36 mg, 0.26 mmol, 1 eq.) was dissolved in dme (2 mL) and added to this solution at room temperature. After stirring the reaction mixture for 2 hours, the solvent was removed in vacuo at room temperature (Yield: not determined).

$^{31}$P{$^1$H}-NMR (101.3 MHz, C$_6$D$_6$): δ=49.2 (s)

13) Preparation of 2-(bis(2,6-dimethoxybenzoyl)phosphoryl)acetic acid ($^{MeO}$BAPO-acetic acid)

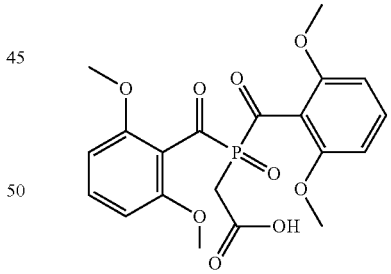

To a solution of $^{MeO}$BAP-acetic acid of example 12 (109 mg, 0.26 mmol, 1 eq.) in ethanol (4 mL), hydrogen peroxide (30%) (0.03 ml, 0.26 mmol, 1 eq.) was added slowly. The reaction mixture was stirred for 30 minutes. Subsequently, the solvent was removed in vacuo and the $^{MeO}$BAPO-acetic acid was once again dissolved in ethanol. After filtration of the sodium bromide the solvent was evaporated in vacuo to yield crystalline $^{MeO}$BAPO-acetic acid (Yield: 78%, 88 mg, 0.20 mmol).

$^{31}$P{$^1$H}-NMR (121.5 MHz, d$^8$-thf): δ=22.2 (s).

14) Preparation of 11-(bis(2,4,6-trimethylbenzoyl)phosphoryl)undecanoic acid (BAPO-undecanoic acid)

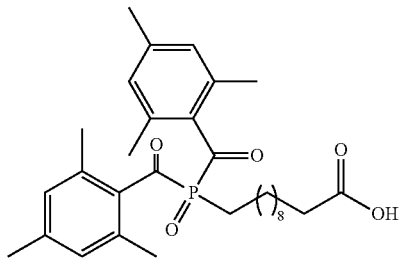

In a 20 mL Schlenk flask sodium bis(mesitoyl)phosphide of example 1 (251.9 mg, 0.724 mmol, 1 eq.) was dissolved in thf (5.00 mL). 11-bromo-undecanoic acid (197.8 mg, 0.72 mmol, 1 eq.) was added and the solution was stirred for two days at 40° C. The white precipitate of sodium bromide was filtered off and the solvent of the yellow filtrate was removed in vacuo at room temperature. The phosphane remains as a yellow oil ($^{31}$P NMR (C$_6$D$_6$, 81.0 MHz): δ=51.5). After solving the phosphane in ethanol, hydrogen peroxide (10%) (0.24 g, 0.72 mmol, 1 eq.) was added and the solution was stirred for 40 minutes at 40° C. The ethanol was evaporated in vacuo at room temperature and the solid pale yellow product was dried in high vacuum (Yield: 312.3 mg, 0.594 mmol, 82%).

$^{31}$P NMR (121.5 MHz, C$_6$D$_6$): δ=18.12 (t, J$_{CP}$=9.8 Hz).

UV/Vis (acetonitrile): 284 nm (max.), 311 nm (max.), 384 nm (max.)

15) Preparation of sodium 2-(bis(2,4,6-trimethylbenzoyl)phosphoryl)acetate (Na-BAPO-acetate)

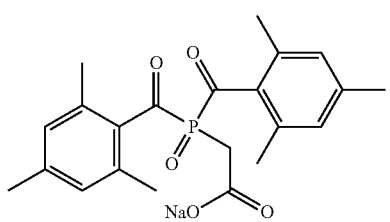

BAPO-acetic acid of example 11 (0.1 g, 0.25 mmol, 1 eq.) was suspended in distilled water (2 mL) and sodium hydrogencarbonate (21.0 mg, 0.25 mmol, 1 eq.) were added. A clear pale yellow solution was obtained. After removing the water in vacuo at room temperature, a pale yellow crystalline powder was isolated (Yield: quantitative). The same procedure can be performed to synthesise other alkali salts of BAPO-acetic acid from carbonates or hydrogencarbonates. (e.g. with potassium hydrogen carbonate, or lithium carbonate).

$^{31}$P NMR (121.5 MHz, D$_2$O): δ=23.6 (t, J=10.8 Hz).

16) Preparation of bis(2,6-dimethoxybenzoyl)-N-piperidinylphosphanoxide

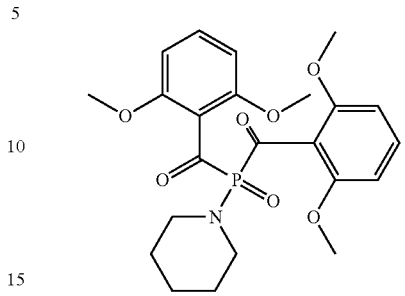

Sodium bis(2,6-dimethoxybenzoyl)phosphide of example 2 (200 mg, 0.52 mmol, 1 eq.) was dissolved in thf (5 mL). Acetic acid (0.03 mL, 0.52 mmol, 1 eq.) was added at room temperature. After stirring the reaction mixture for 2 hours, the solvent was removed in vacuo at room temperature. 2-Propanol (10 mL) was added and the solution was stirred at 70° C. under atmospheric conditions for 80 hours. The solvent was replaced with dichloromethane (5 mL). To this solution triethylamine (0.07 mL, 0.52 mmol, 1 eq.) and piperidine (0.05 mL, 0.52 mmol, 1 eq.) were added. Finally, the reaction mixture was cooled down to 0° C. with an ice-bath and a solution of hexachloroethane (107 mg, 0.52 mmol, 1 eq.) in dichloromethane (5 mL) was added dropwise. The solution was stirred for 2 hours at 0° C. Subsequently, the solvent was removed in vavcuo (Yield: 41%, 0.21 mmol, 96.9 mg).

$^{31}$P NMR (101.3 MHz, C$_6$D$_6$): δ=−4.7 (s).

II) Photoinitiated Emulsion Polymerization

17) Synthesis of poly(vinylacetate) particles

In a Schlenk flask under exclusion of oxygen, 3 mL of a 10% aqueous degassed solution of sodium dodecylsulfate (SDS), 6 mL of degassed and deionised water, 1 mL of an 1% aqueous solution of Na-BAPO-acetate of example 15 and 2 mL of vinylacetate (purification by filtration over MP Alumina N, activity 1, degassed) were mixed. After 5 min. of vigorous stirring (stirrer: RCT Basic, IKA Labortechnik, stage 6) the resulting emulsion was irradiated for 10 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, small portion of the latex were removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently, the sample was kept at 110° C. for 24 h in a drying oven under vacuum (Vacucell, MMM Medcenter GmbH) to remove all volatiles (solvents, unreacted monomer).

In order to isolate the polymer in substance, an aqueous saturated sodium chloride solution was added to the latex. The polymer was isolated by centrifugation (10 min. at 25,000 rpm in a 3K 30 Sigma centrifuge). This procedure was repeated three times to yield a white powder.

Analytic Results:
Dynamic Light Scattering (DLS) (after dilution with water):
Z-average: 35 nm
DLS-PDI=0.16
Solid content: 13.8% (71% conversion).

18) Synthesis of poly(acrylic acid butyl ester) particles

In a Schlenk flask under exclusion of oxygen, 2 mL of a 10% aqueous degassed solution of sodium dodecylsulfate (SDS), 7 mL of degassed and deionised water, 1 mL of an 1% aqueous solution of Na-BAPO-acetate of example 15 and 2 mL of acrylic acid butly ester (purification by filtration over MP Alumina N, activity 1, degassed) were mixed. After 5 min. of vigorous stirring (stirrer: RCT Basic, IKA Labortechnik, stage 6) the resulting emulsion was irradiated for 10 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, a small portion of the latex was removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently, the sample was kept at 110° C. for 24 h in a drying oven under vacuum (Vacucell, MMM Medcenter GmbH) to remove all volatiles (solvents, unreacted monomer).

In order to isolate the polymer in substance, an aqueous saturated sodium chloride solution was added to the latex. The polymer was isolated by centrifugation (10 min. at 25,000 rpm in a 3K 30 Sigma centrifuge). This procedure was repeated three times to yield a white powder.

Analytic Results:
Dynamic Light Scattering (DLS) (after dilution with water):
Z-average: 42 nm
DLS-PDI=0.12
Solid content: 15.7% (92% conversion).

19) Synthesis of poly(para-methylstyrene)particles

In a Schlenk flask under exclusion of oxygen, 50 mg sodium dodecylsulfate (SDS), 10 mL of degassed and deionised water, 0.5 mL of an 1% aqueous solution of Na-BAPO-acetate of example 15 and 3 mL of para-methylstyrene (purification by filtration over MP Alumina N, activity 1, degassed) were mixed. After 5 min. of vigorous stirring (stirrer: RCT Basic, IKA Labortechnik, stage 6) the resulting emulsion was irradiated for 10 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, a small portion of the latex was removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently, the sample was kept at 110° C. for 24 h in a drying oven under vacuum (Vacucell, MMM Medcenter GmbH) to remove all volatiles (solvents, unreacted monomer).

In order to isolate the polymer in substance, a saturated sodium chloride solution in methanol was added to the latex. The polymer was isolated by centrifugation (25,000 rpm in a 3K 30 Sigma centrifuge). This procedure was repeated three times to yield a white powder.

Analytic Results:
Dynamic Light Scattering (DLS) (after dilution with water):
Z-average: 59 nm
DLS-PDI=0.28
Solid content: 16.0% (89% conversion).

20) Synthesis of copolymer particles from styrene/sodium 4-vinyl-benzosulfonate In a Schlenk flask under exclusion of oxygen, 100 mg of sodium 4-vinyl-benzosulfonate, 2 mL of a 10% aqueous degassed solution of sodium dodecylsulfate (SDS), 8 mL of degassed and deionised water, 1 mL of an 1% aqueous solution of Na-BAPO-acetate of example 15 and 2 mL of styrene (purification by filtration over MP Alumina N, activity 1, degassed) were mixed. After 5 min. of vigorous stirring (stirrer: RCT Basic, IKA Labortechnik, stage 6) the resulting emulsion was irradiated for 10 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, a small portion of the latex was removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently, the sample was kept at 110° C. for 24 h in a drying oven under vacuum (Vacucell, MMM Medcenter GmbH) to remove all volatiles (solvents, unreacted monomer).

In order to isolate the polymer in substance, a saturated sodium chloride solution in methanol was added to the latex. The polymer was isolated by centrifugation (10 min. at 25,000 rpm in a 3K 30 Sigma centrifuge). This procedure was repeated three times to yield a white powder.

Analytic Results:
Dynamic Light Scattering (DLS) (after dilution with water):
Z-average: 29 nm
DLS-PDI=0.15
Solid content: 14.6% (74% conversion).

21) Synthesis of copolymer particles from styrene/methacrylic acid butyl ester In a Schlenk flask under exclusion of oxygen, 4 mL of a 10% aqueous degassed solution of sodium dodecylsulfate (SDS), 7 mL of degassed and deionised water, 1 mL of an 1% aqueous solution of Na-BAPO-acetate of example 15, 1.2 mL of styrene (purification by filtration over MP Alumina N, activity 1, degassed), and 0.8 mL of methacrylic acid butyl ester (purification by filtration over MP Alumina N, activity 1, degassed) were mixed. After 5 min. of vigorous stirring (stirrer: RCT Basic, IKA Labortechnik, stage 6) the resulting emulsion was irradiated for 10 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, a small portion of the latex was removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently, the sample was kept at 110° C. for 24 h in a drying oven under vacuum (Vacucell, MMM Medcenter GmbH) to remove all volatiles (solvents, unreacted monomer).

In order to isolate the polymer in substance, an aqueous saturated sodium chloride solution was added to the latex. The polymer was isolated by centrifugation (10 min. at 25,000 rpm in a 3K 30 Sigma centrifuge). This procedure was repeated three times to yield a white powder.

Analytic Results:

Dynamic Light Scattering (DLS) (after dilution with water):

Z-average: 22 nm

DLS-PDI=0.15

Solid content: 15.5% (87% conversion).

22) Synthesis of Copolymer Particles from Styrene/Acrylonitrile

In a Schlenk flask under exclusion of oxygen, 2 mL of a 10% aqueous degassed solution of sodium dodecylsulfate (SDS), 9 mL of degassed and deionised water, 1 mL of an 1% aqueous solution of Na-BAPO-acetate of example 15, 1.6 mL of styrene (purification by filtration over MP Alumina N, activity 1, degassed), and 0.4 mL of acrylnitrile (purification by filtration over MP Alumina N, activity 1, degassed) were mixed. After 5 min. of vigorous stirring (stirrer: RCT Basic, IKA Labortechnik, stage 6) the resulting emulsion was irradiated for 10 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, a small portion of the latex was removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently the sample was kept at 110° C. for 24 h in a drying oven under vacuum (Vacucell, MMM Medcenter GmbH) to remove all volatiles (solvents, unreacted monomer).

In order to isolate the polymer in substance, an aqueous saturated sodium chloride solution was added to the latex. The polymer was isolated by centrifugation (10 min. 25,000 rpm in a 3K 30 Sigma centrifuge). This procedure was repeated three times to yield a white powder.

Analytic Results:

Dynamic Light Scattering (DLS) (after dilution with water):

Z-average: 46 nm

DLS-PDI=0.12; Solid content: 10.0% (58% conversion).

23) Synthesis of copolymer particles from styrene/methacrylic acid glycidyl ester In a Schlenk flask under exclusion of oxygen, 20 mg of Na-BAPO-acetate of example 15, 200 mg of sodium dodecylsulfate (SDS), 12 mL of degassed and deionised water, 1.5 mL of styrene (purification by filtration over MP Alumina N, activity 1, degassed), and 0.5 mL of methacrylacid glycidyl ester (purification by filtration over MP Alumina N, activity 1, degassed) were mixed. After 5 min. of vigorous stirring (stirrer: RCT Basic, IKA Labortechnik, stage 6) the resulting emulsion was irradiated for 10 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, a small portion of the latex was removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently the sample was kept at 110° C. for 24 h in a drying oven under vacuum (Vacucell, MMM Medcenter GmbH) to remove all volatiles.

In order to isolate the polymer in substance, an aqueous saturated sodium chloride solution was added to the latex. The polymer was isolated by centrifugation (10 min. at 25,000 rpm in a 3K 30 Sigma centrifuge). This procedure was repeated three times to yield a white powder.

Analytic Results:

Dynamic Light Scattering (DLS) (after dilution with water):

Z-average: 35 nm

DLS-PDI=0.12

Solid content: 12.7% (95% conversion).

24) Synthesis of poly(styrene) particles with cetyltrimethylammonium bromide (CTAB)

In a Schlenk flask under exclusion of oxygen 12 mg Na-BAPO-acetate of example 15,380 mg of cetyltrimethylammonium bromide (CTAB), 30 mL of degassed and deionised water, and 5 mL of styrene (distilled under reduced pressure, degassed) were mixed. After 5 min. of vigorous stirring (stirrer: RCT Basic, IKA Labortechnik, stage 6) the resulting emulsion was irradiated for 30 min. with a medium pressure mercury lamp (TQ 150 in a DURAN 50 glass mantel, UV-Consulting Peschl) to give a latex. The sample was stirred for another 24 h under an atmosphere of argon and under exclusion of light. Subsequently, a small portion of the latex was removed for the determination of the particle size and the solid content. For the light scattering measurements, 0.1 mL of latex was diluted with 5 mL water. For the determination of the solid content, 1 mL of sample solution was given onto sea sand (carefully dried at 130° C. in a drying oven) in a Petri dish. Subsequently, the sample was kept at 110° C. for 24 h in a drying oven under vacuum (Vacucell, MMM Medcenter GmbH) to remove all volatiles (solvents, unreacted monomer).

In order to isolate the polymer in substance, an aqueous saturated sodium chloride solution was added to the latex. The polymer was isolated by centrifugation (10 min. at 25,000 rpm in a 3K 30 Sigma centrifuge). This procedure was repeated three times to yield a white powder.

Analytic Results:

Dynamic Light Scattering (DLS) (after dilution with water):

Z-average: 63 nm

DLS-PDI=0.18

Solid content: 9.2% (71% conversion).

25) to 27) Synthesis of poly(styrene) particles in the presence of sodium dodecylsulfate, SDS All examples were made according to the following procedure:

Sodium dodecylsulfate (SDS), styrene (10 g), degassed water (33.5 g) and Na-BAPO-acetate of example 15 were mixed. The reaction mixture was stirred vigorously and exposed to irradiation of a medium pressure mercury lamp (TQ 150 in a DURAN 50 glass mantle, UV-Consulting Peschl).

25) Comparison of Particle Size and Polymerisation Time (with Late Quenching)

To study the effect of the irradiation time on the particle size, samples were taken out of the reaction mixture continuously during irradiation. Said samples were put in a flask under argon atmosphere and stirred in the dark for 72 hours minus the irradiation time. After 72 h, the reaction was quenched by adding one drop of an aqueous hydroquinone solution (1%).

SDS: 100 mg, Na-BAPO-acetate of example 15:20 mg

Result: After about one hour of irradiation the yield exceeded 90%, the particle size increased continuously from around 65 nm after 30 min to about 110 nm after 3 h of irradiation.

26) Comparison of Particle Size and Polymerisation Time (with Immediate Quenching)

To study the effect of the irradiation time on the particle size, samples were taken out of the reaction mixture continuously during irradiation. Said samples were immediately quenched by adding one drop of an aqueous hydroquinone solution (1%).

SDS: 100 mg, Na-BAPO-acetate of example 15:20 mg

Result: After about one hour of irradiation the yield exceeded 90%, the particle size was quite constant in the range of around 65 nm to about 70 nm during 3 h of irradiation.

27) Effect of Photoinitiator Concentration

To study the effect of the photoinitiator concentration on the particle size, the reaction mixture was irradiated for 10 min, after which the reaction was immediately quenched with hydroquinone.

SDS: 100 mg, Na-BAPO-acetate of example 15: from 0.1 mg to 20 mg

Result: For 1 to 10 mg of photoinitiator the particle size was at a constant level of about 48 nm; for higher concentrations the particle size decreases constantly to reach around 30 nm at 20 mg of photoinitiator, for 0.1 mg of photoinitiator an initial particle size of 50 nm was observed.

Although the present invention has been described and illustrated with reference to specific embodiments thereof, it is not intended that the present invention be limited to those illustrative embodiments. Those skilled in that art will recognize that variations and modifications can be made without departing from the true scope of the present invention as defined by the claims that follow. It is therefore intended to include within the present invention all such variations and modifications as fall within the scope of the appended claims and equivalents thereof.

What is claimed is:

1. A compound of formula (Ia)

wherein n is 1 or 2, m is 2, $R^1$, if n=1, is $C_6$-$C_{14}$-aryl or heterocyclyl, or
is at least one of $C_1$-$C_{18}$-alkoxy, —$N(R^4)_2$, $C_1$-$C_{18}$-alkyl, $C_2$-$C_{18}$-alkenyl, and $C_7$-$C_{20}$-arylalkyl, wherein the at least one of $C_1$-$C_{18}$-alkoxy, —$N(R^4)_2$, $C_1$-$C_{18}$-alkyl, $C_2$-$C_{18}$-alkenyl, and $C_7$-$C_{20}$-arylalkyl is
not, once, twice or more than twice interrupted by non-successive functional groups selected from the group consisting of —O—, —S—, —$SO_2$—, —SO—, —$SO_2NR^4$—, $NR^4SO_2$—, —$NR^4$—, —$N^+(R^4)_2An^-$—, —CO—, —O(CO)—, (CO)O—, —O(CO)O—, —$NR^4(CO)NR^4$—, $NR^4$(CO)—, —(CO)$NR^4$—, —$NR^4$(CO)O—, —O(CO)$NR^4$—, —Si($R^5$)$_2$—, —OSi($R^5$)$_2$—, —OSi($R^5$)$_2$O—, and —Si($R^5$)$_2$O—,
is not, once, twice or more than twice interrupted by bivalent residues selected from the group consisting of heterocyclo-diyl, heterocyclo-diylium$^+$An$^-$ and $C_6$-$C_{14}$-aryldiyl, and
is not, additionally or alternatively either once, twice or more than twice substituted by substituents selected from the group consisting of halogen, cyano, azido, epoxy, $C_6$-$C_{14}$-aryl, $C_1$-$C_8$-alkyl, $C_1$-$C_8$-alkoxy, $C_2$-$C_8$-alkenyl, $C_1$-$C_8$-alkylthio, $C_7$-$C_{20}$-arylalkyl, hydroxy, —$SO_3M$, —COOM, $PO_3M_2$, —PO(N($R^5$)$_2$)$_2$, PO(O$R^5$)$_2$, —$SO_2N(R^4)_2$, —$N(R^4)_2$, —$N^+(R^4)_3An^-$, heterocyclylium$^+$An$^-$, —$CO_2N(R^5)_2$, —$COR^4$, —$OCOR^4$, —$NR^4$(CO)$R^5$, —(CO)O$R^4$, —$NR^4$(CO)N($R^4$)$_2$, —Si(O$R^5$)$_y$($R^5$)$_{3-y}$, —OSi(O$R^5$)$_y$($R^5$)$_{3-y}$, wherein y=1, 2 or 3, $R^1$, if n=2, is $C_6$-$C_{15}$-aryldiyl, or
is at least one of $C_4$-$C_{18}$-alkanediyl, $C_4$-$C_{18}$-alkenediyl, and $C_4$-$C_{18}$-alkinediyl, wherein the at least one is $C_4$-$C_{18}$-alkanediyl, $C_4$-$C_{18}$-alkenediyl, and $C_4$-$C_{18}$-alkinediyl is
not, once, twice or more than twice interrupted by non-successive groups selected from the group consisting of —O—, —$SO_2$—, —$NR^4$—, —$N^+(R^4)_2An^-$, —CO—, —OCO—, —O(CO)O—, $NR^4$(CO)—, —$NR^4$(CO)O—, O(CO)$NR^4$—, —$NR^4$(CO)$NR^4$—, $C_6$-$C_{15}$-aryl, heterocyclo-diyl and heterocyclo-diylium$^+$An$^-$,
is not, additionally or alternatively either once, twice and more than twice substituted by substituents selected from the group consisting of halogen, cyano, $C_6$-$C_{14}$-aryl, heterocyclyl, heterocyclo-diylium$^+$An$^-$, $C_1$-$C_8$-alkyl, $C_1$-$C_8$-alkoxy, $C_1$-$C_8$-alkylthio, —$SO_3M$, —COOM, $PO_3M_2$, —$N(R^4)_2$, —$N^+(R^4)_3An^-$, —$CO_2N(R^4)_2$, —$OCOR^4$, —O(CO)O$R^4$—, $NR^4$(CO)$R^5$, —$NR^3$(CO)O$R^5$, O(CO)N($R^4$)$_2$, and —$NR^4$(CO)N($R^4$)$_2$, or is bivalent bis($C_6$-$C_{15}$)-aryl, which is not or once interrupted by groups selected from the group consisting of —O—, —S—, $C_4$-$C_{18}$-alkanediyl, and $C_4$-$C_{18}$-alkenediyl, $R^2$ is $C_6$-$C_{14}$-aryl or heterocyclyl, or is at least one of $C_1$-$C_{18}$-alkyl, $C_2$-$C_{18}$-alkenyl, and $C_7$-$C_{20}$-arylalkyl, wherein the at least one of $C_1$-$C_{18}$-alkyl, $C_2$-$C_{18}$-alkenyl, and $C_7$-$C_{20}$-arylalkyl is not, once, twice or more than twice interrupted by non-successive functional groups selected from the group consisting of —O—, —$NR^4$—, —$N^+(R^4)_2An^-$—, —CO—, —OCO—, —O(CO)O—, $NR^4$(CO)—, —$NR^4$(CO)O—, O(CO)$NR^4$—, and —$NR^4$(CO)$NR^4$—, is not, once, twice or more than twice interrupted by bivalent residues selected from the group consisting of heterocyclo-diyl, heterocyclo-diylium$^+An^-$, and $C_6$-$C_{14}$-aryldiyl, and is not, additionally or alternatively either once, twice or more than twice substituted by substituents selected from the group consisting of halogen, cyano, $C_6$-$C_{14}$-aryl, heterocyclyl, $C_1$-$C_8$-alkyl, $C_1$-$C_8$-alkoxy, $C_1$-$C_8$-alkylthio, $C_2$-$C_8$-alkenyl, $C_4$-$C_{15}$-arylalkyl, —COOM, —$SO_3M$, —$PO_3M_2$, —$SO_2N(R^4)_2$, —$NR^4SO_2R^5$, —$N(R^4)_2$—, —$N^+(R^4)_3An^-$, —$CO_2N(R^4)_2$, —$COR^4$—, —$OCOR^5$, —O(CO)$OR^5$, $NR^4$(CO)$R^4$, —$NR^4$(CO)$OR^4$, O(CO)$N(R^4)_2$, and —$NR^4$(CO)$N(R^4)_2$, $R^3$ independently denotes a substituent as defined for $R^1$ if n is 1, whereby $R^4$ is independently selected from the group consisting of hydrogen, $C_1$-$C_8$-alkyl, $C_6$-$C_{14}$-aryl, $C_7$-$C_{15}$-arylalkyl and heterocyclyl, or $N(R^4)_2$ as a whole is an N-containing heterocycle, or $N^+(R^4)_2An^-$ and $N^+(R^4)_3An^-$ as a whole are or contain a cationic N-containing heterocycle with a counteranion, $R^5$ is independently selected from the group consisting of $C_1$-$C_8$-alkyl, $C_6$-$C_{14}$-aryl, $C_7$-$C_{15}$-arylalkyl and heterocyclyl, or $N(R^5)_2$ as a whole is a N-containing heterocycle, or $N^+(R^5)_2An^-$ and $N^+(R^5)_3An^-$ as a whole are or contain a cationic N-containing heterocycle with a counteranion, $An^-$ is a 1/p equivalent of a p-valent anion, the compound contains at least one functional group or substituent selected from the group consisting of —$SO_3M$, —COOM, $PO_3M_2$, —$N^+(R^4)_3An^-$, and heterocyclylium$^+An^-$ and wherein M is a 1/q equivalent of a q-valent metal ion, or is an ammonium ion, or a primary, secondary, tertiary or quaternary organic ammonium ion, or a guanidinium ion.

\* \* \* \* \*